Jan. 24, 1956 M. TANTAU Plant Pat. 1,452
ROSE PLANT
Filed March 11, 1955
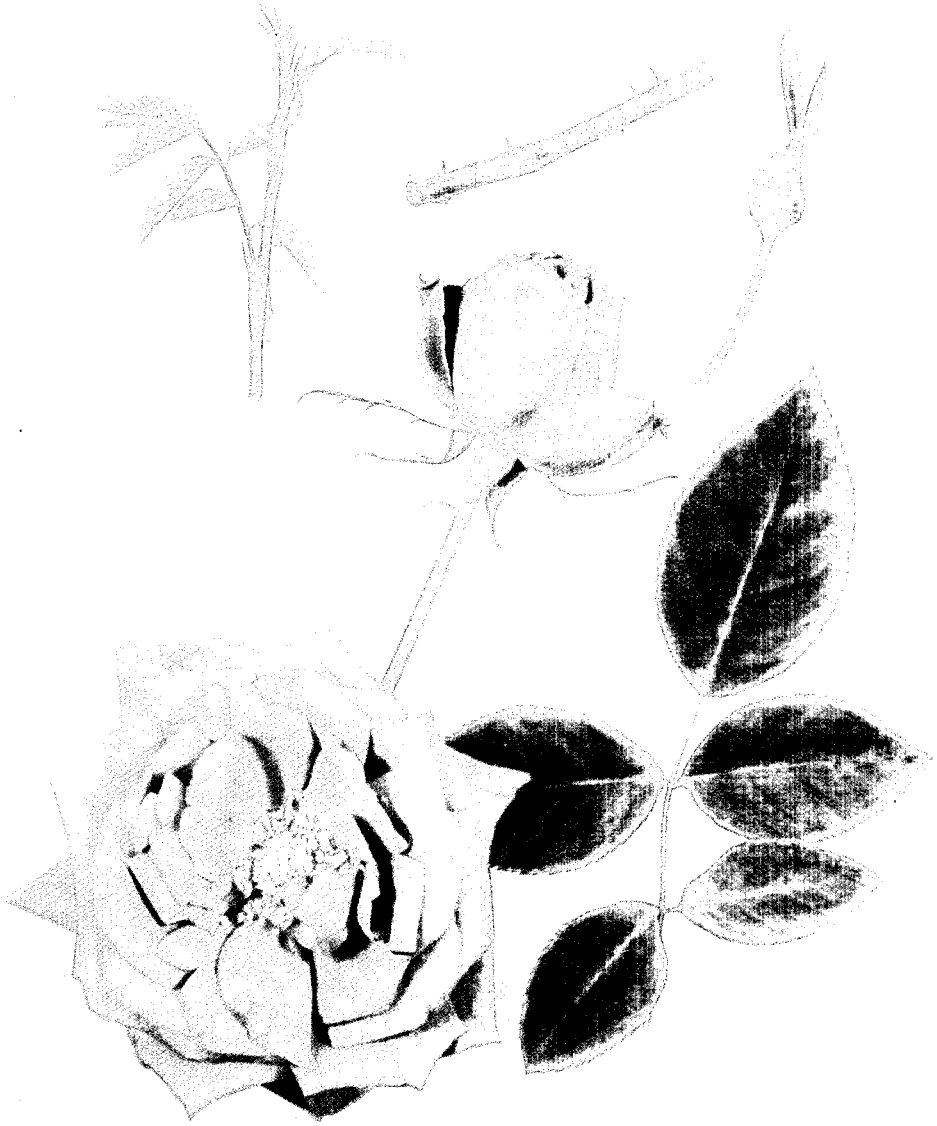
Inventor.
Mathias Tantau
By: Robb & Robb
Attorneys.

United States Patent Office

Plant Pat. 1,452
Patented Jan. 24, 1956

1,452

ROSE PLANT

Mathias Tantau, Uetersen, Holstein, Germany, assignor to Jackson & Perkins Company, Newark, N. Y., a corporation of New York Application March 11, 1955, Serial No. 493,844

1 Claim. (Cl. 47—61)

The present invention relates to a new and distinct variety of rose plant of the hybrid tea class, which was originated by me by crossing the variety "Crimson Glory" (Plant Patent No. 105) with the variety "Hens Verschuren" (unpatented).

The primary objective in making this cross was to produce a new variety of rose plant suitable for cut flowers having the general red color and form of the flowers of "Crimson Glory," combined with the productiveness of "Hens Verschuren." This objective was fully achieved, as evidenced by the following unique combination of outstanding characteristics with which the new variety is endowed as follows:

(1) The vigorous and upright habit of growth of the plant;

(2) The pale yellow green coloring of the foliage which is very prominent in the young foliage and which is quite unusual in a rose of such a dark color;

(3) The hooded sepals;

(4) The cupped form of the flower, which tends to flatten slightly as it matures;

(5) The extremely strong fragrance of the flowers; and (6) The rich Carmine red general color tonality of the flowers, with a light overcast of Spectrum red.

The foregoing characteristics and distinctions definitely differentiate my new variety from its parents, as well as from all other varieties of its class of which I am aware, and asexual production of the variety by budding, as performed at Newark, New York, U. S. A., and also at Pleasanton, California, U. S. A., shows that these characteristics and distinctions come true to form and are established and transmitted through succeeding propagations.

The accompanying drawing shows typical specimens of the foliage, stems and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
*Seed parent.*—"Crimson Glory."
*Pollen parent.*—"Hens Verschuren."
Classification:
*Botanic.*—Hybrid tea.
*Commercial.*—Hybrid tea.

FLOWER (Observations made from specimens grown in a greenhouse at Newark, New York, U. S. A., about midmorning, in the early part of the month of April.)

Blooming habit: Recurrent—continuous.
Bud:
*Size.*—Large.
*Form.*—Globular; is not affected by wet or hot weather.

*Color.*—When sepals first divide—Acajou Red, Plate 13. When petals begin to unfurl—Carmine, Plate 1. When half blown: inside of petals—Carmine, Plate 1, lightly overcast with Spectrum Red, Plate 1; reverse of petals—Carmine, Plate 1, lightly overcast with Nopal Red, Plate 1.
*Sepals.*—Branched; with "hood" above bud; curl back when petals begin to unfurl. Color: Inside—Kildare Green, Plate 31; outside—Oil Green, Plate 5.
*Calyx.*—Color—Lettuce Green, Plate 5. Shape—pear. Size—small. Aspect—smooth. Odor when rubbed—none.
*Peduncle.*—Length—medium. Aspect—smooth. Strength—erect; slender. Color—Oil Green, Plate 5.
*Opening.*—Opens up well; is not affected by adverse weather conditions.
Bloom:
*Size.*—Large. Average size when fully expanded—4 inches.
*Borne.*—Singly and several together.
*Stems.*—Medium length; strong.
*Form—(when first open).*—Cupped. Permanence—flattens slightly as blooms age.
*Petalage.*—Double (full but open center). Number of petals under normal conditions—From 30 to 35.
*Color.*—Center of flower—Carmine, Plate 1, lightly overcast with Spectrum Red, Plate 1. Outer petals—Spectrum Red, Plate 1, lightly overcast with Carmine, Plate 1. Base of petals (aiglet)—Deep Chrome, Plate 3. Inside of petals—Carmine, Plate 1, overcast with Spectrum Red, Plate 1. Reverse of petals—Pomegranate Purple, Plate 12, lightly overcast with Carmine, Plate 1. General tonality from a distance—Carmine, Plate 1, lightly overcast with Spectrum Red, Plate 1.
*Discoloration.*—General tonality at end of first day—Carmine, Plate 1, lightly overcast with Spectrum Red, Plate 1. Second day—Carmine, Plate 1, overcast with Spectrum Red, Plate 1. Third day—Carmine, Plate 1, lightly overcast with Pomegranate Purple, Plate 12.
Petals:
*Texture.*—Thick; is not affected by wet or hot weather.
*Appearance.*—Inside—velvety; outside—satiny.
*Form.*—Oval; slightly notched.
*Arrangement.*—Imbricated (regularly arranged shingle-like.
*Petaloids in center.*—Few; small.
*Persistence.*—Drop off cleanly.
*Fragrance.*—Strong. Nature—very sweet "Old Rose perfume" (Centifolia).
*Lasting quality.*—On plant—long; as cut flower—long.

GENITAL ORGANS

Stamens, anthers: Medium size; many.
*Arrangement.*—Regular around styles.
*Color.*—Light Orange Yellow, Plate 3.
Stamens, filaments (threads): Medium length.
*Color.*—Begonia Rose, Plate 1.
Pollen:
*Color.*—Pale Orange Yellow, Plate 3.
Styles: Loosely separated; uneven length; medium length; thin.
Stigmas:
*Color.*—Cream Buff, Plate 30.
Ovaries: All enclosed in calyx.
Hips: None.
Seeds: None.

PLANT

Form: Bush.
Growth: Vigorous; upright.
Foliage: 5 to 7 leaflets.
*Size.*—Medium.
*Quantity.*—Abundant.
*Color.* — New foliage: upper side — Pale Yellow Green, Plate 6, lightly overcast with Spectrum Red, Plate 1; under side—Spectrum Red, Plate 1, with center overcast slightly with Oil Green, Plate 5. Old foliage: upper side—Cress Green, Plate 31; under side—Light Cress Green, Plate 31.
*Shape.*—Oval pointed.
*Texture.*—Upper side—smooth; under side—smooth.
*Ribs and veins.*—Ordinary.
*Edge.*—Serrated (saw-toothed).
*Serration.*—Both double and single; small.
*Leaf stem.*—Color—Absinthe Green, Plate 31. Under side—prickles.
*Stipules.*—Long; bearded.
Wood:
*New wood.*—Color—Lettuce Green, Plate 5. Bark—smooth.
*Old wood.*—Color—Cress Green, Plate 31. Bark—smooth.

Thorns:
*Thorns.*—Quantity: On main stalks from base—many; on laterals from stalk—many. Form—narrow base; medium length; some straight and some hooked downward. Color (when young)—Venetian Pink, Plate 13. Position—irregular.
*Prickles.*—Quantity: on main stalks—none; on laterals—none.
*Short needles.*—Quantity: on main stalks—none; on laterals—none.

I claim:

A new and distinct variety of rose plant of the hybrid tea class, substantially as herein shown and described, characterized particularly as to novelty by its vigorous and upright growth, by the unusual pale yellow green color of its foliage which is very prominent in the young foliage, its hooded sepals, its cupped flowers which flatten slightly with age, the extremely strong fragrance of its flowers, and the rich Carmine red, lightly overcast with Spectrum red, general color tonality of its flowers.

No references cited.